United States Patent [19]

Sommer et al.

[11] 4,029,742

[45] June 14, 1977

[54] PROCESS OF PRODUCING MADDRELL SALT

[75] Inventors: Klaus Sommer, Heidelberg; Hermann Weber, Hemsbach, both of Germany

[73] Assignee: Benckiser-Knapsack GmbH, Ladenburg (Neckar), Germany

[22] Filed: Apr. 6, 1976

[21] Appl. No.: 674,123

[30] Foreign Application Priority Data

Apr. 9, 1975 Germany .......................... 2515370

[52] U.S. Cl. ................................ 423/314; 423/305
[51] Int. Cl.² ................... C01B 15/16; C01B 25/26
[58] Field of Search ................... 423/305, 314, 315

[56] References Cited

UNITED STATES PATENTS 3,230,041   1/1966   Edwards et al. .................. 423/305

FOREIGN PATENTS OR APPLICATIONS 1,050,908   12/1966   Germany .......................... 423/315

Primary Examiner—O. R. Vertiz
Assistant Examiner—Gregory A. Heller
Attorney, Agent, or Firm—Erich M. H. Radde

[57] ABSTRACT

An advantageous process of producing Maddrell salt which is substantially free of water-soluble by-products is described. The resulting substantially water-insoluble Maddrell salt is especially useful as polishing and cleaning agent in toothpaste.

12 Claims, No Drawings

PROCESS OF PRODUCING MADDRELL SALT

BACKGROUND OF THE INVENTION

1. Field of the Invention

The present invention relates to a process of producing Maddrell salt, i.e. a long-chain, high-molecular weight sodium polyphosphate and more particularly to a simple and highly advantageous process of producing said salt in a form which is substantially free of water-soluble by-products and to such a substantially water-insoluble Maddrell salt.

2. Description of the Prior Art

Heretofore, Maddrell salt has been produced by heating sodium orthophosphate of disodium pyrophosphate at a temperature between 250° C. and 350° C. However, only little attention has been paid to its preparation since due to its insolubility in water no utility has been found therefor. This is also the reason why no quantitative investigations regarding the amount and the type of its water-soluble components — which always are obtained when producing the salt according to the methods known and used heretofore — were carried out. The water-soluble components of said salt were simply eluted with water to produce a salt useful for scientific investigations.

However, a few years ago Maddrell salt has been found to be useful on a large scale as polishing and cleaning agent in toothpastes. For such a use the salt should have as low a water-soluble component as possible. When dehydrating mon-sodium orthophosphate in the known manner to Maddrell salt, there are always formed thereby the water-soluble compounds sodium trimetaphosphate and di-sodium pyrophosphate in an amount depending almost exclusively on the manner in which the temperature is adjusted during dehydration. Usually the amount of water-soluble components exceeds 5%. Said water-soluble compounds have an extremely negative effect upon the consistency, effectiveness, and stability on storage of the toothpaste containing Maddrell salt.

In the meantime, several new processes of producing Maddrell salt have become known. Thus a process for producing Maddrell salt with up to 4% of water-soluble components is described in U.S. Pat. No. 2,356,799. According to this process, monosodium orthophosphate must be shaped to pellets in a first reaction step. Said pellets are then converted into Maddrell salt by heating to a temperature between 300° C. and 460° C. This mode of operation, however, is quite complicated and expensive because an additional process step of producing pellets is required.

Furthermore, it is stated in "Journal American Chemical Society" vol. 81, p. 79 (1959) that neither pelletizing nor very fine comminution of monosodium orthophosphate or considerably prolonged thermal treatment are able to reduce the water-soluble portion in the final product below 5% calculated for total substance.

J. R. Van Wazer in his book on "Phosphorus and its compounds" vol. 1, p. 668, has disclosed that, when converting monosodium orthophosphate to Maddrell salt at a temperature of 400° C., water vapor is formed by splitting off the water of constitution. Such formation of water vapor may even have a negative effect upon the formation of Maddrell salt.

German Published Application No. 1,667,569 describes a process of producing Maddrell salt from monosodium orthophosphate by heating the latter to 450° C. and removing by suction the water vapor formed due to the condensation reaction. The water vapor partial pressure is maintained during this reaction between 50 Torr. and 450 Torr.

As described in "Zeitschrift Anorg. Allg. Chemie", vol. 258, p. 52 (1949) and in "Analytical Chemistry", vol. 30, p. 1101 to 1110 (1958), Maddrell salt is produced by heating monosodium orthophosphate to a temperature of 350° C. or, respectively, 380° C. within a period of time between about 50 hours and about 168 hours. Thereby, a product is obtained which is contaminated to a considerable extent. It must be purified by washing out the by-products.

Another process of producing Maddrell salt is described in German Pat. No. 2,161,600. Said process consists in dehydrating monosodium orthophosphate at a temperature between about 300° C. and about 380° C. in the presence of water vapor. According to this process dehydration is carried out in a saturated water vapor atmosphere. This process is also rather complicated since it is necessary that a predetermined water vapor partial pressure is maintained during dehydration.

SUMMARY OF THE INVENTION

It is one object of the present invention to provide a simple, highly effective, and advantageous process of producing Maddrell salt by dehydration of monosodium orthophosphate and/or di-sodium pyrophosphate which process can be carried out in a simple manner and without having to maintain a predetermined water vapor partial pressure.

Another object of the present invention is to provide a substantially pure Maddrell salt containing water-soluble compounds in an amount not exceeding about 2% and more particularly to provide a Maddrell salt which is substantially free of water-soluble compounds.

Other objects of the present invention and advantageous features thereof will become apparent as the description proceeds.

In principle, and in contrast to the heretofore known processes, the Maddrell salt according to the present invention is produced in a simple manner and without having to maintain a predetermined water vapor partial pressure by heating monosodium orthophosphate or, respectively, di-sodium pyrophosphate at a temperature between about 250° C. and about 450° C. with the addition of a salt of phosphoric acid with a nitrogen-containing base. Said phosphoric acid salts with nitrogen-containing bases are added to the dehydration charge in catalytic amounts between about 0.25% and about 5.0% by weight, of the starting material. The mixture is then heated and calcined. When proceeding in this manner, a Maddrell salt is obtained, the water-soluble components of which do not exceed about 2%, by weight. This low content of water-soluble components does not increase even on comminuting and grinding the salt, so that it is not necessary to subsequently temper the same or condition it by heating.

As stated above, phosphoric acid salts of nitrogen-containing bases are added when carrying out the process according to the present invention. Especially useful salts of this type are, for instance, ammonium dihydrogen orthophophate, di-ammonium hydrogen orthophosphate, urea phosphate, guanidine phosphate, melaminephosphate, hydroxylammonium phosphate, hydrazine phosphate, or ammonium polyphosphate.

These compounds can be added to the charge of monosodium orthophosphate and/or di-sodium pyrophosphate either as such or in mixture with each other, preferably in amounts between about 0.5% and about 2.0%.

It is an especially noteworthy advantage of the process according to the present invention that the nature and quality of the starting material is substantially of no importance. Thus, the same satisfactory results are achieved regardless whether a starting material is used which has been obtained by the spray-drying process or by crystallization. For instance, when starting with a spray-dried monosodium orthophosphate, the amount of catalyst an be added thereto already before spray-drying, provided the phosphoric acid salts of the nitrogen-containing bases as they are used in this process, are not sensitive to the spray-drying temperature. If a starting material is used which has been obtained by crystallization, the phosphoric acid salts of the nitrogen-containing bases can either be admixed to the starting material by means of a simple mixing device or they can be sprayed subsequently upon the starting material in the form of an aqueous solution or of an alcoholic solution or of a solution in a mixture of water and alcohol.

This process can be carried out, for instance, in a kneading device which can be heated, in a rotating cylindrical kiln which is directly heated, or in a rotating drum. When using a rotating kiln or furnace, the process can be carried out especially advantageously by making use of the so-called recirculation process, whereby part of the finished product is returned to the rotating kiln or oven. The advantage of this mode of operation is to be seen in the feature that it is possible to keep the amount of recirculated finished material and of the charge of freshly introduced starting mixture at such a proportion that adhering on and/or sticking of the reaction product to the rotating kiln or furnace and agglomeration during calcination can be prevented. When using a kneading device or a rotating kiln, calcination can be effected continuously. Most preferably, the temperature during calcination is kept between about 300° C. and about 420° C.

It is, of course, also possible to carry out the process in batch procedure by calcining the starting mixture in a muffle or retort furnace.

In conclusion, the advantage of the process according to the present invention over the known processes consists in the feature that a Maddrell salt is produced the water-soluble portion of which is below 2.0%, even after comminution and grinding and that neither subsequent tempering nor maintaining a pre-determined water vapor partial pressure is required. Furthermore, the process can be carried out continuously, of course, depending upon the apparatus used.

DESCRIPTION OF THE PREFERRED EMBODIMENTS

The following examples serve to illustrate the present invention without, however, limiting the same thereto.

EXAMPLE 1

200 g. of spray-dried monosodium orthophosphate of a pH-value of 4.5 are well mixed with 2 g. (1%) of finely pulverized ammonium dihydrogen orthophosphate. The resulting mixture is heated in an electrically heated oven at an oven temperature of 400° C. for a period of time of 1½ hours. After cooling and grinding, a Maddrell salt of a purity of 99.2% is obtained.

EXAMPLE 2

200 g. of spray-dried monosodium orthophosphate of a pH-value of 4.5 are intimately mixed with 2 g. (1%) of finely pulverized hydroxylammonium phosphate. The mixture is calcined at 400° C. within a period of time of about 2 hours as described in Example 1. The water-soluble component of the resulting cooled and comminuted Maddrell salt amounts to 1.1%.

EXAMPLE 3

4 g. (2%) of finely pulverized urea phosphate are admixed to 200 g. of spray-dried monosodium orthophosphate. The mixture is heated in an electrically heated oven at an oven temperature of 400° C. for a period of 2 hours. After cooling and grinding, the product has a Maddrell salt content of 98.1%.

EXAMPLE 4

A mixture of 500 kg. of spray-dried monosodium orthophosphate of a pH-value of 4.5 and of 5 kg. of finely pulverized ammonium dihydrogen orthophosphate is calcined in continuous operation by passing through a kneading device which is indirectly heated by means of oil. The temperature of the heat carrier is 330° C. The reaction product remains in the kneading device for about 4½ hours. The resulting comminuted product has a content of 98.8% of Maddrell salt.

EXAMPLE 5

A rotating kiln is charged by means of a dosing groove or chute and a feed screw with 70 kg. to 100 kg./hour of a mixture of 500 kg. of spray-dried sodium dihydrogen phosphate of a pH-value of 4.5 and 10 kg. of finely pulverized ammonium dihydrogen phosphate. The temperature of the heating gas introduced into the rotating kiln or furnace is between about 430° C. and about 480° C. The temperature at the gas outlet is between about 100° C. and about 130° C. The charge remains in the rotating kiln or oven for about 45 minutes. The resulting Maddrell salt, after cooling and comminution, contains water-soluble components only in an amount of 1.8%.

Of course, many changes and variations in the calcination temperature and duration, in the apparatus used for calcination, in the kind of phosphoric acid salt of nitrogen containing bases admixed to the sodium dihydrogen phosphate and/or di-sodium pyrophosphate, in the amounts of said salts added to the charge, and the like may be made by those skilled in the art in accordance with the principles set forth herein and in the claims annexed hereto.

We claim:

1. In a process of producing Maddrell salt, including the steps of heating a starting material selected from the group consisting of mono-sodium orthophosphate, di-sodium pyrophosphate, and mixtures thereof, to a temperature between about 250° C. and about 450° C., whereby said starting material is converted to Maddrell salt, and recovering the Maddrell salt formed, the improvement which comprises carrying out said heating step with an admixture of said starting material and a phosphoric acid salt of a nitrogen-containing base in a catalytically effective amount of between about 0.25% and about 5.0%, by weight, of the starting material, whereby the Maddrell salt containing less than about 2% water-soluble impurities is formed.

2. The process of claim 1, in which the phosphoric acid salt of a nitrogen-containing base is a salt selected from the group consisting of ammonium dihydrogen orthophosphate, di-ammonium hydrogen orthophosphate, urea phosphate, guanidine phosphate, melamine phosphate, hydroxylammonium phosphate, hydrazine phosphate, ammonium polyphosphate, and mixtures thereof.

3. The process of claim 1, in which the amount of phosphoric acid salt of a nitrogen-containing base added to the starting material is between about 0.5% and about 2.0% of said starting material.

4. The process of claim 2, in which the amount of phosphoric acid salt of a nitrogen-containing base added to the starting material is between about 0.5% and about 2.0% of said starting material.

5. The process of claim 1, in which the calcination temperature is between about 300° C. and about 420° C.

6. The process of claim 2, in which the calcination temperature is between about 300° C. and about 420° C.

7. The process of claim 1, further comprising the step of admixing said phosphoric acid salt with said starting material prior to said heating step.

8. The process of claim 1, further comprising the step of recycling a portion of the Maddrell salt from said recovery step to said heating step.

9. The process of claim 1, wherein said heating temperature is between about 300° C. and 420° C.

10. The process of claim 2, wherein said phosphoric acid salt comprises ammonium dihydrogen orthophosphate.

11. The process of claim 2, wherein said phosphoric acid salt comprises hydroxylammonium phosphate.

12. The process of claim 2, wherein said phosphoric acid salt comprises urea phosphate.

* * * * *

UNITED STATES PATENT OFFICE
CERTIFICATE OF CORRECTION

Patent No. 4,029,742                    Dated    June 14, 1977

Inventor(s) Klaus Sommer et al.

It is certified that error appears in the above-identified patent and that said Letters Patent are hereby corrected as shown below:

Column 1, line 15:   "of" should read -- or --.

Column 1, line 31:   "mon-sodium" should read -- mono-sodium --.

Column 3, line 14:   "an" should read -- can --.

Signed and Sealed this twenty-third Day of August 1977

[SEAL]

Attest:

RUTH C. MASON
Attesting Officer

C. MARSHALL DANN
Commissioner of Patents and Trademarks